United States Patent
Wu et al.

(10) Patent No.: US 9,982,313 B2
(45) Date of Patent: May 29, 2018

(54) COMPOSITIONS AND METHODS FOR DETECTION OF HERPES SIMPLEX VIRUS 1 AND 2

(75) Inventors: Xiaoning Wu, Fremont, CA (US); Karen Young, San Ramon, CA (US)

(73) Assignee: Roche Molecular Systems, Inc., Pleasanton, CA (US)

( * ) Notice: Subject to any disclaimer, the term of this patent is extended or adjusted under 35 U.S.C. 154(b) by 136 days.

(21) Appl. No.: 13/588,943

(22) Filed: Aug. 17, 2012

(65) Prior Publication Data

US 2014/0051590 A1   Feb. 20, 2014

(51) Int. Cl.
  *C12Q 1/70* (2006.01)
  *C12Q 1/68* (2018.01)
(52) U.S. Cl.
  CPC ............. *C12Q 1/705* (2013.01); *C12Q 1/686* (2013.01); *C12Q 2600/16* (2013.01)
(58) Field of Classification Search
  None
  See application file for complete search history.

(56) References Cited

U.S. PATENT DOCUMENTS

| | | | |
|---|---|---|---|
| 6,958,210 B2 | 10/2005 | Smith et al. | |
| 7,291,488 B2 | 11/2007 | Wolfe et al. | |
| 7,667,025 B2 | 2/2010 | Smith et al. | |
| 7,893,241 B2 | 2/2011 | Smith et al. | |
| 7,947,820 B2 | 5/2011 | Wolfe et al. | |
| 8,221,976 B2 | 7/2012 | Wolfe et al. | |
| 2006/0252032 A1 | 11/2006 | Aslanukov et al. | |
| 2007/0141559 A1* | 6/2007 | Exner ................ | C12Q 1/705 435/5 |
| 2009/0191538 A1* | 7/2009 | Donegan ............ | C12Q 1/708 435/5 |
| 2010/0184018 A1* | 7/2010 | Smith et al. ....... | 435/5 |

FOREIGN PATENT DOCUMENTS

WO  2002061390 A2  8/2002

OTHER PUBLICATIONS

Blast analysis( documents included).*
Lowe et al. Nucleic Acids Research, vol. 18, No. 7, p. 1757-1761,1990.*
GenBank GU734771 [online] Apr. 27, 2010 [retrieved on Sep. 6, 2015] retrieved from http://www.ncbi.nlm.nih.gov/nuccore/gu734771.*
GenBank Z86099 [online] Nov. 14, 2006 [retrieved on Sep. 6, 2015] retrieved from http://www.ncbi.nlm.nih.gov/nuccore/z86099.*
Xu et al. Seroprevalence and Coinfection with Herpes Simplex Virus Type 1 and Type 2 in the United States, 1988-1994. (JID 185:1019-24 (2002).*
Lo, Y.M. Dennis. Introduction to the Polymerase Chain Reaction. In: Clinical Applications of PCR. Humana Press, pp. 3-10 (1998).*
Bio-Rad. Real-Time PCR Applications Guide, Bulletin 5279 (2006).*
Molenkamp et al. Real-Time Multiplex PCR of five Different DNA Targets Using the LightCycler 480 System. Biochemica 3:15-17 (2007).*
Dolan, Aidan, et al., 1998, "The Genome Sequence of Herpes Simplex Virus Type 2", Journal of Virology, 72 (3):2010-2021.
McGeoch, D. J., et al., 1988, "The Complete DNA Sequence of the Long Unique Region in the Genome of Herpes Simplex Virus Type 1", Journal of General Virology, 69:1531-1574.
PCT/EP2013/067087, Oct. 9, 2013, International Search Report.
Altuglu, I., et al., 2006, "Comparison of different polymerase chain reaction methods for detection of herpes simplex virus types 1 and 2 encephalitis", European Journal of Clinical Microbiology & Infectious Diseases, 25:669-671.
Hyun-Jin Kim, et al., 2011, "A rapid and simple isothermal nuclei acid amplification test for detection of herpes simplex virus types 1 and 2", Journal of Clinical Virology, 50:26-30.
Legoff, Jerome, et al., 2006, "Real-Time PCR Quantification of Genital Shedding of Herpes Simplex Virus (HSV) and Human Immunodeficiency Virus (HIV) in Women Coinfected with HSV and HIV", Journal of Clinical Microbiology, 44(2):423-432.
Sankuntaw, Nipaporn, 2011, "Single tube multiplex real-time PCR for the rapid detection of herpesvirus infections of the central nervous system", Molecular and Cellular Probes, 25:114-120.
Offce Action dated Oct. 27, 2016 to European Application No. 13748353.3.
Database Geneseq [Online] Feb. 22, 2007 (Feb. 22, 2007), "Herpes simplex virus type 2 thymidine kinase gene portion, SEQ ID No. 7.", retrieved from EBI accession No. GSN:AEM18196, Database accession No. AEM18196.

* cited by examiner

*Primary Examiner* — Samuel C Woolwine
(74) *Attorney, Agent, or Firm* — David J. Chang; M. Reza Savari

(57) ABSTRACT

Methods for the rapid detection of the presence or absence of Herpes simplex virus 1 and 2 (HSV-1 and HSV-2) in a biological or non-biological sample are described. The methods can include performing an amplifying step, a hybridizing step, and a detecting step. Furthermore, primers, probes targeting the genes for HSV-1 viral DNA polymerase B (HSV-1 Pol) and HSV-1 thymidine kinase C (HSV-1 TK), and also target the genes for HSV-2 thymidine kinase C (HSV-2 TK) and HSV-2 glycoprotein B (HSV-2 gB), along with kits are provided that are designed for the detection of HSV-1 and/or HSV-2.

4 Claims, 7 Drawing Sheets

| | HSV-1 | | | |
|---|---|---|---|---|
| TK-A | | | | |
| | Prob | vp/PCR | l95_conc | u95_conc |
| | 0.95 | 27.82 | . | . |
| Pol-B | | | | |
| | Prob | vp/PCR | l95_conc | u95_conc |
| | 0.95 | 11.00 | 6.25 | 38.15 |
| TK-C | | | | |
| | Prob | vp/PCR | l95_conc | u95_conc |
| | 0.95 | 7.17 | 4.88 | 14.72 |

FIGURE 7

| | HSV-2 | | | |
|---|---|---|---|---|
| gB3 | | | | |
| | Prob | vp/PCR | l95_conc | u95_conc |
| | 0.95 | 3.62 | 2.75 | 6.97 |
| Pol-B | | | | |
| | Prob | vp/PCR | l95_conc | u95_conc |
| | 0.95 | 7.80 | 4.63 | 24.60 |
| TK-C | | | | |
| | Prob | vp/PCR | l95_conc | u95_conc |
| | 0.95 | 5.01 | 3.23 | 12.71 |

FIGURE 8

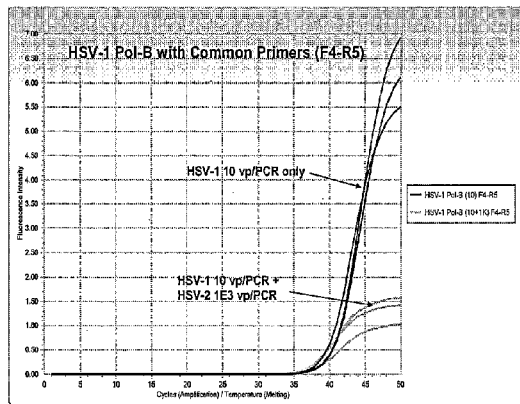
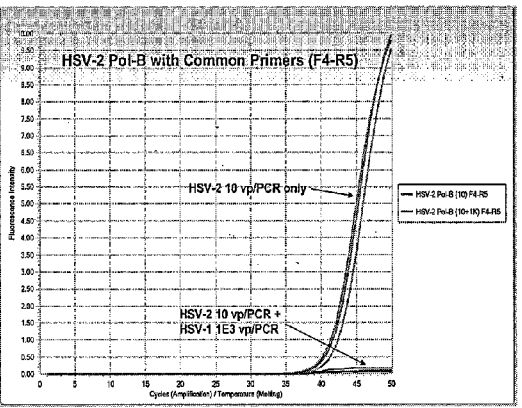
FIGURE 9A　　　　　　　　FIGURE 9B
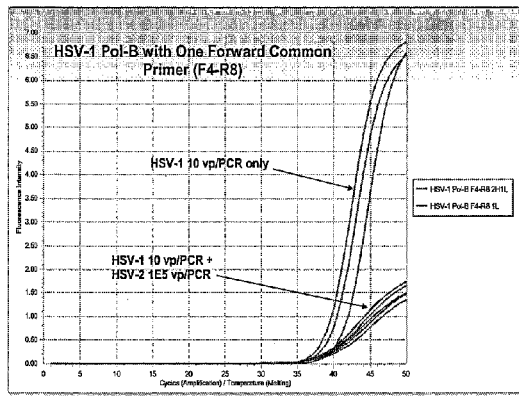
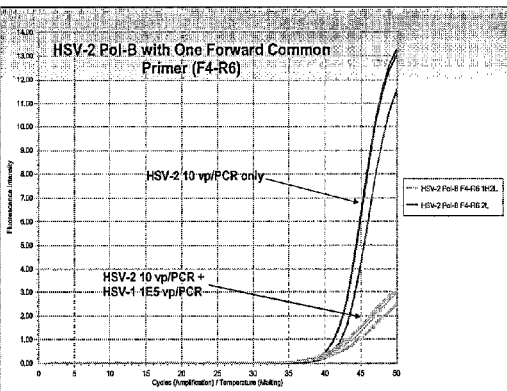
FIGURE 10A　　　　　　　　FIGURE 10B

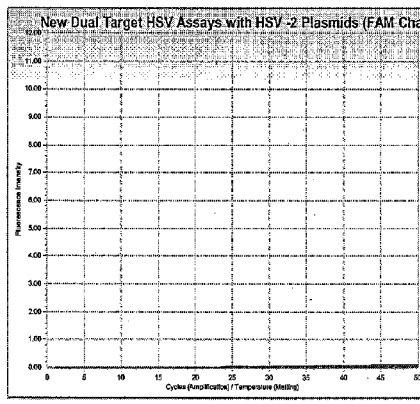
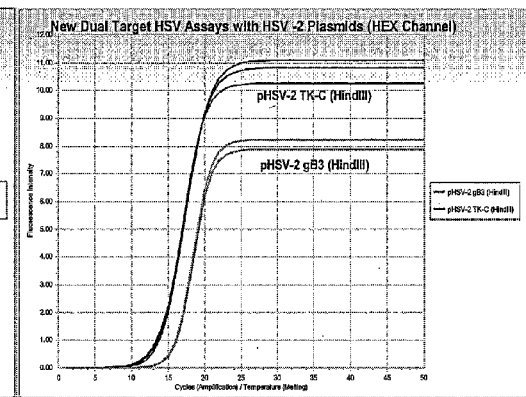

FIGURE 13A              FIGURE 13B

| Virus Name | Form | Testing Concentration | | Ct Value | | |
|---|---|---|---|---|---|---|
| | | | | HSV-1 | HSV-2 | IC |
| Cytomegalovirus (HHV-5) | Viral DNA | 9.6E+06 | c/mL | NaN | NaN | 39.8 |
| HHV-6B (Roseolovirus) | Viral DNA | 1.4E+06 | TCID50/mL | NaN | NaN | 38.9 |
| HHV-7 (Roseolovirus) | Viral DNA | 1.1E+06 | TCID50/mL | NaN | NaN | 39.2 |
| HHV-8 (Roseolovirus) | Viral DNA | 4.2E+04 | TCID50/mL | NaN | NaN | 39.7 |
| Varicella Zoster Virus (Strain 275, Cell Line MRC-5) | Viral particle | 2.3E+07 | c/mL | NaN | NaN | 39 |
| Varicella Zoster Virus (Strain Isolate D, Cell Line CV-1) | Viral particle | 2.5E+04 | TCID50/mL | NaN | NaN | 38.6 |

FIGURE 14

COMPOSITIONS AND METHODS FOR DETECTION OF HERPES SIMPLEX VIRUS 1 AND 2

FIELD OF THE INVENTION

The present invention relates to the field of virus diagnostic, and more particularly, to detection of the Herpes simplex virus 1 and/or 2.

BACKGROUND OF THE INVENTION

Herpes simplex virus 1 and 2 (HSV-1 and HSV-2), also known as human herpes virus 1 and 2 (HHV-1 and -2), are enveloped double-stranded DNA viruses and belong to the herpes virus family, Herpesviridae. Generally, the HSV virus infects humans in the skin or mucous membranes of the mouth (HSV-1) and genitals (HSV-2). The HSV virus is capable of establishing life-long latent infections after the primary infections, and reactivating from latency for new outbreaks. HSV infections generally involve eruption of tiny blisters on the skin or mucous membranes, after which the virus remains in a dormant state inside nerve cells supplying the infected area. The virus undergoes cycles of re-activation in which the virus travels through the nerve fibers back to the skin and thereby causes eruptions of blisters in the same area of skin as the earlier infection. There are also cases not involving the formation of blisters.

HSV is the causative agent of a variety of disorders, including blindness and encephalitis. If left untreated, the mortality rate for the latter disease is as high as 70%, as opposed to only 19% among those who receive treatment. About 38% of the treated patients recover completely, which underscores the importance of diagnosing HSV infection at an early stage. HSV-1 mostly causes adult encephalitis, whereas HSV-2 more commonly causes newborn encephalitis, the latter being associated with maternal genital infections. Furthermore, HSV-2 is one of the most common sexually transmitted diseases in society. The fatality rate of HSV-related encephalitis is higher than that of all other types of encephalitis, being 1 to 4 per million per year. The large variety of its symptoms may include fever, headaches, seizures, an altered level of consciousness, and personality changes.

Traditionally, it is believed that HSV-1 causes oral infection, while HSV-2 causes genital infection. However, HSV-1 is a more frequent cause of primary genital herpes and often co-infects with HSV-2 in many developed countries. As a result, it becomes very important to have a PCR assay that is capable to detect and discriminate both viruses simultaneously. This new HSV assay is designed to accomplish that in a single reaction tube.

Diagnosis of HSV-1 and/or HSV-2 (HSV-1/2) infections is commonly performed using cell culture on appropriate clinical specimens, which is time consuming and labor intensive. In addition, serologic diagnosis of HSV-1/2 infections lacks sufficient sensitivity and specificity. Thus there is a need in the art for a quick and reliable method to specifically detect both types of HSV in a sensitive manner.

SUMMARY OF THE INVENTION

Embodiments of the present invention relates to methods for the rapid detection of the presence or absence of HSV-1 and/or HSV-2 in a biological or non-biological sample, for example, multiplex detection of HSV-1 and/or HSV-2 by real-time polymerase chain reaction in a single test tube. Embodiments include methods of detection of HSV-1/2 comprising performing at least one cycling step, which may include an amplifying step and a hybridizing step. Furthermore, embodiments include primers, probes, and kits that are designed for the detection of single HSV-1 or HSV-2, or HSV-1 and HSV-2 co-infections in a single tube. The detection methods are designed to target the genes for HSV-1 viral DNA polymerase B (HSV-1 Pol) and HSV-1 thymidine kinase C(HSV-1 TK), and also target the genes for HSV-2 thymidine kinase C(HSV-2 TK) and HSV-2 glycoprotein B (HSV-2 gB) simultaneously, which allows one to detect and differentiate HSV-1 and/or HSV-2 infections in a singlet test.

In one embodiment, a method of detecting HSV-1 and/or HSV-2 in a sample is provided, including performing an amplifying step including contacting the sample with a plurality of sets of HSV-1 and HSV-2 primers to produce one or more amplification products if any HSV-1 and/or HSV-2 nucleic acid is present in the sample; performing a hybridizing step including contacting the one or more amplification products with a plurality of detectable HSV-1 and HSV-2 probes; and detecting the presence or absence of the one or more amplification products, wherein the presence of the one or more amplification products is indicative of the presence of HSV-1 and/or HSV-2 in the sample and wherein the absence of the one or more amplification products is indicative of the absence of HSV-1 and/or HSV-2 in the sample; wherein the plurality of sets of HSV-1 and HSV-2 primers include HSV-1 primer sets that amplify an HSV-1 Pol and an HSV-1 TK gene targets, and HSV-2 primer sets that amplify an HSV-2 TK and an HSV-2 gB gene targets, and wherein said plurality of detectable HSV-1 and HSV-2 probes include HSV-1 probes specific for an HSV-1 Pol and an HSV-1 TK amplification products, HSV-2 probes specific for an HSV-2 TK and an HSV-2 gB amplification products.

In one embodiment, the primer set for amplification of the HSV-1 Pol gene target include nucleic acid sequences of SEQ ID NOs: 1 and 2 or a complement thereof, the primer set for amplification of the HSV-1 TK gene target include nucleic acid sequences of SEQ ID NOs: 4 and 5 or a complement thereof, the primer set for amplification of the HSV-2 TK gene target include nucleic acid sequences of SEQ ID NOs: 7 and 8 or a complement thereof, and the primer set for amplification of the HSV-2 gB gene target include nucleic acid sequences of SEQ ID NOs: 10 and 11 or a complement thereof, and wherein the detectable of HSV-1 probe for detection of the HSV-1 Pol amplification product includes the nucleic acid sequence of SEQ ID NO: 3 or a complement thereof, the detectable of HSV-1 probe for detection of the HSV-1 TK amplification product includes the nucleic acid sequence of SEQ ID NO: 6 or a complement thereof, the detectable of HSV-2 probe for detection of the HSV-2 TK amplification product includes the nucleic acid sequence of SEQ ID NO: 9 or a complement thereof, the detectable of HSV-2 probe for detection of the HSV-2 gB amplification product includes the nucleic acid sequences of SEQ ID NO: 12 or a complement thereof.

Other embodiment of the present invention provide an oligonucleotide comprising or consisting of a sequence of nucleotides selected from SEQ ID NOs: 1, 2, 3, 4, 5, 6, 7, 8, 9, 10, 11, and 12, or a complement thereof, which oligonucleotide has 100 or fewer nucleotides. In another aspect, the present invention provides an oligonucleotide that includes a nucleic acid having at least 70% sequence identity (e.g., at least 75%, 80%, 85%, 90% or 95%, etc.) to one of SEQ ID NOs: 1, 2, 3, 4, 5, 6, 7, 8, 9, 10, 11, and 12, or a complement thereof, which oligonucleotide has 100 or fewer nucleotides. Generally, these oligonucleotides may be primer nucleic acids, probe nucleic acids, or the like in these embodiments. In certain of these embodiments, the oligonucleotides have 40 or fewer nucleotides (e.g. 35 or fewer nucleotides, 30 or fewer nucleotides, etc.) In some embodiments, the oligonucleotides comprise at least one modified nucleotide, e.g. to alter nucleic acid hybridization stability relative to unmodified nucleotides. Optionally, the oligonucleotides comprise at least one label and/or at least one quencher moiety. In some embodiments, the oligonucleotides include at least one conservatively modified variation. "Conservatively modified variations" or, simply, "conservative variations" of a particular nucleic acid sequence refers to those nucleic acids, which encode identical or essentially identical amino acid sequences, or, where the nucleic acid does not encode an amino acid sequence, to essentially identical sequences. One of skill will recognize that individual substitutions, deletions or additions which alter, add or delete a single amino acid or a small percentage of amino acids (typically less than 5%, more typically less than 4%, 2% or 1%) in an encoded sequence are "conservatively modified variations" where the alterations result in the deletion of an amino acid, addition of an amino acid, or substitution of an amino acid with a chemically similar amino acid.

In one aspect, amplification can employ a polymerase enzyme having 5' to 3' exonuclease activity. Thus, the first and second fluorescent moieties may be within no more than 5 nucleotides of each other along the length of the probe. In another aspect, the HSV-1 and HSV-1 probes includes a nucleic acid sequence that permits secondary structure formation. Such secondary structure formation generally results in spatial proximity between the first and second fluorescent moiety. According to this method, the second fluorescent moiety on the probe can be a quencher.

In still another aspect, the invention provides for methods of detecting the presence or absence of HSV-1 and/or HSV-2 in a biological sample from an individual. Such methods generally include performing at least one cycling step, which includes an amplifying step and a dye-binding step. Typically, the amplifying step includes contacting the sample with a plurality of pairs of HSV-1/2 primers to produce one or more HSV-1/2 amplification products if a HSV-1 and/or HSV-2 nucleic acid molecule is present in the sample and the dye-binding step includes contacting the HSV-1/2 amplification product with a double-stranded DNA binding dye. Such methods also include detecting the presence or absence of binding of the double-stranded DNA binding dye into the amplification product, wherein the presence of binding is indicative of the presence of HSV-1/2 in the sample, and wherein the absence of binding is indicative of the absence of HSV-1/2 in the sample. A representative double-stranded DNA binding dye is ethidium bromide. In addition, such methods also can include determining the melting temperature between the HSV-1/2 amplification product and the double-stranded DNA binding dye, wherein the melting temperature confirms the presence or absence of HSV-1 and/or HSV-2.

In a further embodiment, a kit for detecting one or more nucleic acids of HSV-1 and/or HSV-2 is provided. The kit can include a plurality of sets of HSV-1 and HSV-2 primers specific for amplification of an HSV-1 Pol and an HSV-1 TK gene targets, and an HSV-2 TK and an HSV-2 gB gene targets; and a plurality of detectable HSV-1 and HSV-2 probes specific for detection of an HSV-1 Pol and an HSV-1 TK amplification products, and an HSV-2 TK and an HSV-2 gB amplification products.

In one aspect, the kit can include probes already labeled with donor and corresponding acceptor fluorescent moieties, or can include fluorophoric moieties for labeling the probes. The kit can also include nucleoside triphosphates, nucleic acid polymerase, and buffers necessary for the function of the nucleic acid polymerase. The kit can also include a package insert and instructions for using the primers, probes, and fluorophoric moieties to detect the presence or absence of HSV-1 and/or HSV-2 in a sample.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In addition, the materials, methods, and examples are illustrative only and not intended to be limiting. All publications, patent applications, patents, and other references mentioned herein are incorporated by reference in their entirety. In case of conflict, the present specification, including definitions, will control.

The details of one or more embodiments of the invention are set forth in the accompanying drawings and the description below. Other features, objects, and advantages of the invention will be apparent from the drawings and detailed description, and from the claims.

BRIEF DESCRIPTION OF THE FIGURES

FIG. 7 shows assay analytical sensitivity of three independent HSV-1 assays (Pol-B, TK-A, and TK-C) by Probit analysis.

FIG. 8 shows assay analytical sensitivity of three independent HSV-2 assays (gB3, Pol-B, and TK-C) by Probit analysis.

FIGS. 9A and 9B show target competition with common PCR primers in presence of both targets.

FIGS. 10A and 10B show target competition with single common PCR primers in presence of both targets.

FIGS. 13A and 13B show cross reactivity analysis of the dual target HSV-1/2 assay with HSV-2 plasmids.

FIG. 14 shows a table of cross reactivity of HSV-1/2 assay with other closely related herpes viruses.

DETAILED DESCRIPTION OF THE INVENTION

Figures 1A, 1B:
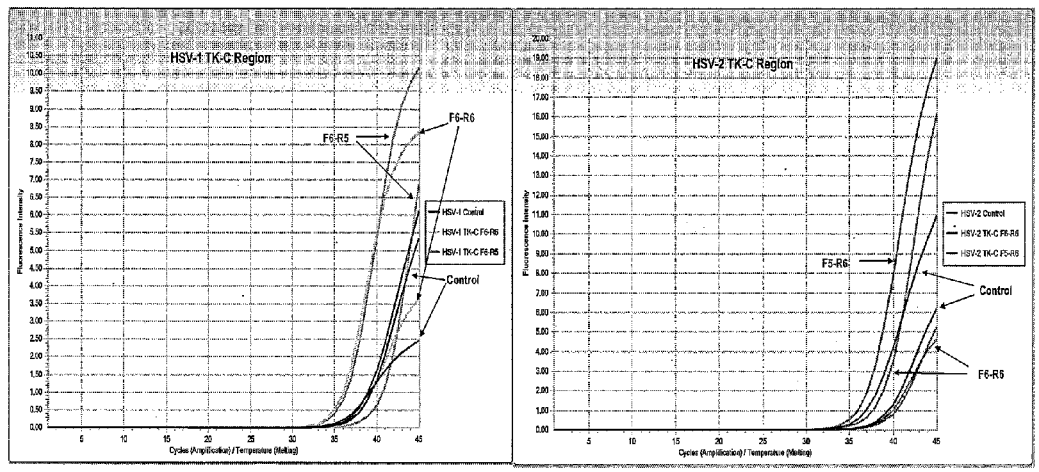
FIG. 1A shows PCR growth curves of experiments using primers that worked well in HSV-1 TK-C region.
FIG. 1B shows PCR growth curves of experiments using primers that worked well in HSV-2 TK-C region.

Diagnosis of HSV-1 and/or HSV-2 infections by nucleic acid amplification provides a method for rapidly and accurately detecting viral infections. A real-time assay for detecting HSV-1/2 in a sample is described herein. Primers and probes for detecting HSV-1/2 are provided, as are articles of manufacture or kits containing such primers and probes. The increased sensitivity of real-time PCR for detection of HSV-1/2 compared to other methods, as well as the improved features of real-time PCR including sample containment and real-time detection of the amplified product, make feasible the implementation of this technology for routine diagnosis of HSV-1/2 infections in the clinical laboratory.

The methods may include performing at least one cycling step that includes amplifying one or more portions of HSV-1 Pol and an HSV-1 TK nucleic acid molecule gene targets, and an HSV-2 TK and an HSV-2 gB nucleic acid molecule gene targets from a sample using a plurality of pairs of primers, including HSV-1 Pol primers, HSV-1 TK primers, HSV-2 TK primers, and HSV-2 gB primers. "HSV-1 Pol primers", "HSV-1 TK primer", "HSV-2 TK primer", and "HSV-2 gB primer" as used herein refer to oligonucleotide primers that specifically anneal to nucleic acid sequences encoding HSV-1 Pol, HSV-1 TK, HSV-2 TK, and HSV-2 gB, respectively, and initiate synthesis therefrom under appropriate conditions. Each of the discussed HSV-1 and HSV-2 primers anneals to a target within or adjacent to the respective HSV-1 Pol, HSV-1 TK, HSV-2 TK, and HSV-2 gB target nucleic acid molecule such that at least a portion of each amplification product contains nucleic acid sequence corresponding to respective target. The one or more of HSV-1 Pol, HSV-1 TK, HSV-2 TK, and HSV-2 gB amplification products are produced provided that one or more of HSV-1 Pol, HSV-1 TK, HSV-2 TK, and HSV-2 gB nucleic acid is present in the sample, thus the presence of the one or more of HSV-1 Pol, HSV-1 TK, HSV-2 TK, and HSV-2 gB amplification products is indicative of the presence of HSV-1 and/or HSV-2 in the sample. The amplification product should contain the nucleic acid sequences that are complementary to one or more detectable probes for HSV-1 Pol, HSV-1 TK, HSV-2 TK, and HSV-2 gB. Each cycling step includes an amplification step, a hybridization step, and a detection step, in which the sample is contacted with the one or more detectable probes for HSV-1 Pol, HSV-1 TK, HSV-2 TK, and HSV-2 gB for detection of the presence or absence of HSV-1 and/or HSV-2 in the sample.

Embodiments of the HSV-1/2 detection methods are capable to detect and discriminate both HSV-1 and HSV-2 viral types in a single PCR tube, and in addition, utilize a dual target approach for target detection. This dual target approach provides certain advantages. For example, unknown mutations at HSV-1/2 primer and probe binding sites can occur, such that the HSV-1/2 detection assay performance might be potentially compromised. To minimize such a risk in the embodiments of the present invention, two separate gene regions are selected to be the PCR targets for each of HSV-1 and HSVI-2 viral types, that is, HSV-1 Pol and HSV-1 TK for HSV-1 and HSV-2 TK and HSV-2 gB for HSV-2. Because the chance is fairly low that unknown mutations occur at primer and probe binding sites in two separate gene regions at the same time, the assay performance of the presently claimed dual target HSV-1/2 detection methods are less likely to be negatively impacted by unknown mutations.

The methods described here can simultaneously detect both HSV-1 and HSV-2, and discriminate them in a single PCR reaction. The methods can use of viral type specific primers and probes which can avoid the target competition when both HSV-1 and HSV-2 coexist in a single sample, but have different viral titers. The primers and probes used for detection of HSV-1/2 do not have cross reactivity, not only between HSV-1 and HSV-2 viral types, but also with other closely related herpes viruses. Furthermore, the dual target approach used in embodiments of the present HSV-1/2 detection methods can minimize the potential negative impact on the assay performance due to unknown mutations at the primer and probe binding sites.

As used herein, the term "amplifying" refers to the process of synthesizing nucleic acid molecules that are complementary to one or both strands of a template nucleic acid molecule (e.g., HSV-1 DNA Pol, HSV-1 TK, HSV-2 TK, and HSV-2 gB nucleic acid molecules). Amplifying a nucleic acid molecule typically includes denaturing the template nucleic acid, annealing primers to the template nucleic acid at a temperature that is below the melting temperatures of the primers, and enzymatically elongating from the primers to generate an amplification product. Amplification typically requires the presence of deoxyribonucleoside triphosphates, a DNA polymerase enzyme (e.g., Platinum® Taq) and an appropriate buffer and/or co-factors for optimal activity of the polymerase enzyme (e.g., $MgCl_2$ and/or KCl).

The term "primer" is used herein as known to those skilled in the art and refers to oligomeric compounds, primarily to oligonucleotides but also to modified oligonucleotides that are able to "prime" DNA synthesis by a template-dependent DNA polymerase, i.e., the 3'-end of the, e.g., oligonucleotide provides a free 3'-OH group whereto further "nucleotides" may be attached by a template-dependent DNA polymerase establishing 3' to 5' phosphodiester linkage whereby deoxynucleoside triphosphates are used and whereby pyrophosphate is released. Therefore, there is—except possibly for the intended function—no fundamental difference between a "primer", an "oligonucleotide", or a "probe" according to the invention.

The term "hybridizing" refers to the annealing of one or more probes to an amplification product. Hybridization conditions typically include a temperature that is below the melting temperature of the probes but that avoids non-specific hybridization of the probes.

The term "5' to 3' exonuclease activity" refers to an activity of a nucleic acid polymerase, typically associated with the nucleic acid strand synthesis, whereby nucleotides are removed from the 5' end of nucleic acid strand.

The term "thermostable polymerase" refers to a polymerase enzyme that is heat stable, i.e., the enzyme catalyzes the formation of primer extension products complementary to a template and does not irreversibly denature when subjected to the elevated temperatures for the time necessary to effect denaturation of double-stranded template nucleic acids. Generally, the synthesis is initiated at the 3' end of each primer and proceeds in the 5' to 3' direction along the template strand. Thermostable polymerases have been isolated from *Thermus fiavus, T. ruber, T. thermophilus, T. aquaticus, T. lacteus, T. rubens, Bacillus stearothermophilus*, and *Methanothermus fervidus*. Nonetheless, polymerases that are not thermostable also can be employed in PCR assays provided the enzyme is replenished.

The term "complement thereof" refers to nucleic acid that is both the same length as, and exactly complementary to, a given nucleic acid.

The term "extension" or "elongation" when used with respect to nucleic acids refers to when additional nucleotides (or other analogous molecules) are incorporated into the nucleic acids. For example, a nucleic acid is optionally extended by a nucleotide incorporating biocatalyst, such as a polymerase that typically adds nucleotides at the 3' terminal end of a nucleic acid.

The terms "identical" or percent "identity" in the context of two or more nucleic acid sequences, refer to two or more sequences or subsequences that are the same or have a specified percentage of nucleotides that are the same, when compared and aligned for maximum correspondence, e.g., as measured using one of the sequence comparison algorithms available to persons of skill or by visual inspection. Exemplary algorithms that are suitable for determining percent sequence identity and sequence similarity are the BLAST programs, which are described in, e.g., Altschul et al. (1990) "Basic local alignment search tool" *J. Mol. Biol.* 215:403-410, Gish et al. (1993) "Identification of protein coding regions by database similarity search" Nature Genet. 3:266-272, Madden et al. (1996) "Applications of network BLAST server" Meth. Enzymol. 266:131-141, Altschul et al. (1997) "Gapped BLAST and PSI-BLAST: a new generation of protein database search programs" *Nucleic Acids Res.* 25:3389-3402, and Zhang et al. (1997) "PowerBLAST: A new network BLAST application for interactive or automated sequence analysis and annotation" *Genome Res.* 7:649-656, which are each incorporated herein by reference.

A "modified nucleotide" in the context of an oligonucleotide refers to an alteration in which at least one nucleotide of the oligonucleotide sequence is replaced by a different nucleotide that provides a desired property to the oligonucleotide. Exemplary modified nucleotides that can be substituted in the oligonucleotides described herein include, e.g., a C5-methyl-dC, a C5-ethyl-dC, a C5-methyl-dU, a C5-ethyl-dU, a 2,6-diaminopurine, a C5-propynyl-dC, a C5-propynyl-dU, a C7-propynyl-dA, a C7-propynyl-dG, a C5-propargylamino-dC, a C5-propargylamino-dU, a C7-propargylamino-dA, a C7-propargylamino-dG, a 7-deaza-2-deoxyxanthosine, a pyrazolopyrimidine analog, a pseudo-dU, a nitro pyrrole, a nitro indole, 2'-0-methyl Ribo-U, 2'-0-methyl Ribo-C, an N4-ethyl-dC, an N6-methyl-dA, and the like. Many other modified nucleotides that can be substituted in the oligonucleotides of the invention are referred to herein or are otherwise known in the art. In certain embodiments, modified nucleotide substitutions modify melting temperatures (Tm) of the oligonucleotides relative to the melting temperatures of corresponding unmodified oligonucleotides. To further illustrate, certain modified nucleotide substitutions can reduce non-specific nucleic acid amplification (e.g., minimize primer dimer formation or the like), increase the yield of an intended target amplicon, and/or the like in some embodiments of the invention. Examples of these types of nucleic acid modifications are described in, e.g., U.S. Pat. No. 6,001,611, which is incorporated herein by reference.

HSV-1 and HSV-2 Nucleic Acids and Oligonucleotides

The invention provides methods to detect HSV-1 and/or HSV-2 by amplifying, for example, a portion of one or more of the HSV-1 Pol and HSV-1 TK nucleic acid sequences, and the HSV-2 TK and HSV-2 gB nucleic acid sequences. Nucleic acid sequences from HSV-1 and/or HSV-2 are available (see, for example, GenBank Accession Nos. M10792 for HSV-1 Pol; J02224 for HSV-1 TK; HQ123137 for HSV-2 TK; and HM011358 for HSV-2 gB). Specifically, primers and probes to amplify and detect HSV-1 Pol and an HSV-1 TK nucleic acid molecule targets, and an HSV-2 TK and an HSV-2 gB nucleic acid molecule targets are provided by the embodiments of the present invention.

For detection of HSV-1 and/or HSV-2, primers and probes to amplify HSV-1 Polymerase and HSV-1 TK nucleic acid sequences, and the HSV-2 TK and HSV-2 gB nucleic acid molecules are provided. HSV-1/2 nucleic acids other than those exemplified herein can also be used to detect HSV-1/2 in a sample. For example, functional variants can be evaluated for specificity and/or sensitivity by those of skill in the art using routine methods. Representative functional variants can include, e.g., one or more deletions, insertions, and/or substitutions in the HSV-1/2 nucleic acids disclosed herein.

More specifically, embodiments of the oligonucleotides of the present invention each include a nucleic acid with a sequence selected from SEQ ID NOs: 1, 2, 3, 4, 5, 6, 7, 8, 9, 10, 11, and 12, a substantially identical variant thereof in which the variant has at least, e.g., 80%, 90%, or 95% sequence identity to one of SEQ ID NOs: 1, 2, 3, 4, 5, 6, 7, 8, 9, 10, 11, and 12, or a complement of SEQ ID NOs: 1, 2, 3, 4, 5, 6, 7, 8, 9, 10, 11, and 12 and the variant.

TABLE I

HSV-1 DNA Polymerase Primers and Probe

| SEQ ID NO | | SEQUENCE |
|---|---|---|
| 1 | Forward Primer (F11) | 5'- GACAACTTCTGCCCGGCCATCAA -3' |
| 2 | Reverse Primer (R8) | 5'- TCGCTGGATGTCCCGAAGGCCA -3' |
| 3 | Probe | 5'- CGGAACAACACGCTAGCCCAGCCGCGGGCC -3' |

TABLE II

HSV-1 HSV-1 Thymidine Kinase Primers and Probe

| SEQ ID NO | | SEQUENCE |
|---|---|---|
| 4 | Forward Primer (F6) | 5'- CGTCTTTATCCTGGATTACGACCAATC -3' |
| 5 | Reverse Primer (R5) | 5'- GGTCGCAGATCGTCGGTATGGA -3' |
| 6 | Probe | 5'- CTGCAACTTACCTCCGGGATGGTCCAGACC -3' |

TABLE III

HSV-2 HSV-1 Thymidine Kinase Primers and Probe

| SEQ ID NO | | SEQUENCE |
|---|---|---|
| 7 | Forward Primer (F5) | 5'- TCCTTCCGATGCATCTATTTGTCC -3' |
| 8 | Reverse Primer (R6) | 5'- ATGGACCCGGCGGTTGTGA -3' |

TABLE III-continued

HSV-2 HSV-1 Thymidine Kinase Primers and Probe

| SEQ ID NO | | SEQUENCE |
|---|---|---|
| 9 | Probe | 5'- TTGCGCCTCACCGCCGGGATGATCCCAAC -3' |

TABLE IV

HSV-2 Glycoprotein B Primers and Probe

| SEQ ID NO | | SEQUENCE |
|---|---|---|
| 10 | Forward Primer (F7) | 5'- CGCTACGTCCTGCAACTGCAAC -3' |
| 11 | Reverse Primer (R7) | 5'- GGCCGACACCAAAGCCATATATCGGA -3' |
| 12 | Probe | 5'- TCCGCTCACCACCAAGGAACTCAAGACTTCCGACCC -3' |

In one embodiment of the invention, the above described four sets of HSV-1 and/or HSV-2 primers and probes are used in order to provide for detection of HSV-1 and/or HSV-2 in a biological sample suspected of containing HSV-1/2. The sets of primers and probes may comprise or consist the primers and probes specific for the HSV-1 Pol and HSV-1 TK nucleic acid sequences, and also the HSV-2 TK and HSV-2 gB nucleic acid sequences, comprising or consisting of the nucleic acid sequences of SEQ ID NOs: 1, 2, 3, 4, 5, 6, 7, 8, 9, 10, 11, and 12. In another embodiment of the invention, the primers and probes for the HSV-1 and HSV-1 targets comprise or consist of a functionally active variant of any of the primers of SEQ ID NOs: 1, 2, 3, 4, 5, 6, 7, 8, 9, 10, 11, and 12.

A functionally active variant of any of the primers and/or probes of SEQ ID NOs: 1, 2, 3, 4, 5, 6, 7, 8, 9, 10, 11, and 12 may be identified by using the primers and/or probes in the method of the invention. A functionally active variant of a primer and/or probe of any of the SEQ ID NOs: 1, 2, 3, 4, 5, 6, 7, 8, 9, 10, 11, and 12 pertains to a primer which provides a similar or higher specificity and sensitivity in the method or kit of the invention as compared to the respective sequence of SEQ ID NOs: 1, 2, 3, 4, 5, 6, 7, 8, 9, 10, 11, and 12.

The variant may, e.g., vary from the sequence of SEQ ID NOs: 1, 2, 3, 4, 5, 6, 7, 8, 9, 10, 11, and 12 by one or more nucleotide additions, deletions or substitutions such as one or more nucleotide additions, deletions or substitutions at the 5' end and/or the 3' end of the respective sequence of SEQ ID NOs: 1, 2, 3, 4, 5, 6, 7, 8, 9, 10, 11, and 12. As detailed above, a primer (and/or probe) may be chemically modified, i.e., a primer and/or probe may comprise a modified nucleotide or a non-nucleotide compound. A probe (or a primer) is then a modified oligonucleotide. "Modified nucleotides" (or "nucleotide analogs") differ from a natural "nucleotide" by some modification but still consist of a base or base-like compound, a pentofuranosyl sugar or a pentofuranosyl sugar-like compound, a phosphate portion or phosphate-like portion, or combinations thereof. For example, a "label" may be attached to the base portion of a "nucleotide" whereby a "modified nucleotide" is obtained. A natural base in a "nucleotide" may also be replaced by, e.g., a 7-desazapurine whereby a "modified nucleotide" is obtained as well. The terms "modified nucleotide" or "nucleotide analog" are used interchangeably in the present application. A "modified nucleoside" (or "nucleoside analog") differs from a natural nucleoside by some modification in the manner as outlined above for a "modified nucleotide" (or a "nucleotide analog").

Oligonucleotides including modified oligonucleotides and oligonucleotide analogs that amplify a nucleic acid molecule encoding the HSV-1 Pol and HSV-1 TK nucleic acid sequences, and the HSV-2 TK and HSV-2 gB nucleic acid sequences, e.g., nucleic acids encoding alternative portions of HSV-1 Pol and HSV-1 TK, the HSV-2 TK, and HSV-2 gB can be designed using, for example, a computer program such as OLIGO (Molecular Biology Insights Inc., Cascade, Colo.). Important features when designing oligonucleotides to be used as amplification primers include, but are not limited to, an appropriate size amplification product to facilitate detection (e.g., by electrophoresis), similar melting temperatures for the members of a pair of primers, and the length of each primer (i.e., the primers need to be long enough to anneal with sequence-specificity and to initiate synthesis but not so long that fidelity is reduced during oligonucleotide synthesis). Typically, oligonucleotide primers are 8 to 50 nucleotides in length (e.g., 8, 10, 12, 14, 16, 18, 20, 22, 24, 26, 28, 30, 32, 34, 36, 38, 40, 42, 44, 46, 48, or 50 nucleotides in length).

In addition to a set of primers, the methods of the invention may use one or more probes in order to detect the presence or absence of HSV-1 and/or HSV-2. The term "probe" refers to synthetically or biologically produced nucleic acids (DNA or RNA), which by design or selection, contain specific nucleotide sequences that allow them to hybridize under defined predetermined stringencies specifically (i.e., preferentially) to "target nucleic acids", in the present case to a HSV-1 and/or HSV-2 (target) nucleic acid. A "probe" can be referred to as a "detection probe" meaning that it detects the target nucleic acid.

In some embodiments of the present invention, the described HSV-1 and/or HSV-2 probes can be labeled with at least one fluorescent label. In one embodiment, the HSV-1 and/or HSV-2 probes can be labeled with a donor fluorescent moiety, e.g., a fluorescent dye, and a corresponding acceptor fluorescent moiety, e.g., a quencher.

In one embodiment, the probes comprise or consist of a fluorescent moiety and the nucleic acid sequences comprise or consist of SEQ ID NOs: 3, 6, 9, and 12 (shown without the label).

Designing oligonucleotides to be used as hybridization probes can be performed in a manner similar to the design of primers. Embodiments of the present invention may use a single probe or a pair of probes for detection of the amplification product. Depending on the embodiment, the probe(s) use may comprise at least one label and/or at least one quencher moiety. As with the primers, the probes usually have similar melting temperatures, and the length of each probe must be sufficient for sequence-specific hybridization to occur but not so long that fidelity is reduced during synthesis. Oligonucleotide probes are generally 15 to 30 (e.g., 16, 18, 20, 21, 22, 23, 24, or 25) nucleotides in length.

Constructs of the present invention can include vectors each containing one of an HSV-1 Pol, an HSV-1 TK, an HSV-2 TK, and an HSV-2 gB nucleic acid molecule (e.g., SEQ ID NOs: 1, 2, 3, 4, 5, 6, 7, 8, 9, 10, 11, and 12). Constructs of the invention can be used, for example, as control template nucleic acid molecules. Vectors suitable for use in the present invention are commercially available and/or produced by recombinant nucleic acid technology methods routine in the art. HSV-1 and/or HSV-2 nucleic acid molecules can be obtained, for example, by chemical synthesis, direct cloning from HSV-1 and HSV-2, or by PCR amplification.

Constructs suitable for use in the methods of the invention typically include, in addition to the HSV-1 and/or HSV-2 nucleic acid molecules (e.g., a nucleic acid molecule that contains one or more sequences of SEQ ID NOs: 1, 2, 3, 4, 5, 6, 7, 8, 9, 10, 11, and 12), sequences encoding a selectable marker (e.g., an antibiotic resistance gene) for selecting desired constructs and/or transformants, and an origin of replication. The choice of vector systems usually depends upon several factors, including, but not limited to, the choice of host cells, replication efficiency, selectability, inducibility, and the ease of recovery.

Constructs of the invention containing HSV-1 and/or HSV2 nucleic acid molecules can be propagated in a host cell. As used herein, the term host cell is meant to include prokaryotes and eukaryotes such as yeast, plant and animal cells. Prokaryotic hosts may include *E. coli, Salmonella typhimurium, Serratia marcescens*, and *Bacillus subtilis*. Eukaryotic hosts include yeasts such as S. cerevisiae, S. pombe, *Pichia pastoris*, mammalian cells such as COS cells or Chinese hamster ovary (CHO) cells, insect cells, and plant cells such as *Arabidopsis thaliana* and *Nicotiana tabacum*. A construct of the invention can be introduced into a host cell using any of the techniques commonly known to those of ordinary skill in the art. For example, calcium phosphate precipitation, electroporation, heat shock, lipofection, microinjection, and viral-mediated nucleic acid transfer are common methods for introducing nucleic acids into host cells. In addition, naked DNA can be delivered directly to cells (see, e.g., U.S. Pat. Nos. 5,580,859 and 5,589,466).

Polymerase Chain Reaction (PCR)

U.S. Pat. Nos. 4,683,202, 4,683,195, 4,800,159, and 4,965,188 disclose conventional PCR techniques. PCR typically employs two oligonucleotide primers that bind to a selected nucleic acid template (e.g., DNA or RNA). Primers useful in the embodiments of the present invention include oligonucleotides capable of acting as a point of initiation of nucleic acid synthesis within the described HSV-1/2 nucleic acid sequences (e.g., SEQ ID NOs: 1, 2, 4, 5, 7, 8, 10, and 11). A primer can be purified from a restriction digest by conventional methods, or it can be produced synthetically. The primer is preferably single-stranded for maximum efficiency in amplification, but the primer can be double-stranded. Double-stranded primers are first denatured, i.e., treated to separate the strands. One method of denaturing double stranded nucleic acids is by heating.

If the template nucleic acid is double-stranded, it is necessary to separate the two strands before it can be used as a template in PCR. Strand separation can be accomplished by any suitable denaturing method including physical, chemical or enzymatic means. One method of separating the nucleic acid strands involves heating the nucleic acid until it is predominately denatured (e.g., greater than 50%, 60%, 70%, 80%, 90% or 95% denatured). The heating conditions necessary for denaturing template nucleic acid will depend, e.g., on the buffer salt concentration and the length and nucleotide composition of the nucleic acids being denatured, but typically range from about 90° C. to about 105° C. for a time depending on features of the reaction such as temperature and the nucleic acid length. Denaturation is typically performed for about 30 sec to 4 min (e.g., 1 min to 2 min 30 sec, or 1.5 min).

If the double-stranded template nucleic acid is denatured by heat, the reaction mixture is allowed to cool to a temperature that promotes annealing of each primer to its target sequence on the described HSV-1/2 nucleic acid molecules. The temperature for annealing is usually from about 35° C. to about 65° C. (e.g., about 40° C. to about 60° C.; about 45° C. to about 50° C.). Annealing times can be from about 10 sec to about 1 min (e.g., about 20 sec to about 50 sec; about 30 sec to about 40 sec). The reaction mixture is then adjusted to a temperature at which the activity of the polymerase is promoted or optimized, i.e., a temperature sufficient for extension to occur from the annealed primer to generate products complementary to the template nucleic acid. The temperature should be sufficient to synthesize an extension product from each primer that is annealed to a nucleic acid template, but should not be so high as to denature an extension product from its complementary template (e.g., the temperature for extension generally ranges from about 40° C. to about 80° C. (e.g., about 50° C. to about 70° C.; about 60° C.). Extension times can be from about 10 sec to about 5 min (e.g., about 30 sec to about 4 min; about 1 min to about 3 min; about 1 min 30 sec to about 2 min).

PCR assays can employ HSV-1/2 nucleic acid such as RNA or DNA (cDNA). The template nucleic acid need not be purified; it may be a minor fraction of a complex mixture, such as HSV-1/2 nucleic acid contained in human cells. HSV-1/2 nucleic acid molecules may be extracted from a biological sample by routine techniques such as those described in *Diagnostic Molecular Microbiology: Principles and Applications* (Persing et al. (eds), 1993, American Society for Microbiology, Washington D.C.). Nucleic acids can be obtained from any number of sources, such as plasmids, or natural sources including bacteria, yeast, viruses, organelles, or higher organisms such as plants or animals.

The oligonucleotide primers (e.g., SEQ ID NOs: 1, 2, 4, 5, 7, 8, 10, and 11) are combined with PCR reagents under reaction conditions that induce primer extension. For example, chain extension reactions generally include 50 mM KCl, 10 mM Tris-HCl (pH 8.3), 15 mM $MgCl_2$, 0.001% (w/v) gelatin, 0.5-1.0 µg denatured template DNA, 50 pmoles of each oligonucleotide primer, 2.5 U of Taq polymerase, and 10% DMSO). The reactions usually contain 150 to 320 µM each of dATP, dCTP, dTTP, dGTP, or one or more analogs thereof.

The newly synthesized strands form a double-stranded molecule that can be used in the succeeding steps of the reaction. The steps of strand separation, annealing, and elongation can be repeated as often as needed to produce the desired quantity of amplification products corresponding to the target HSV-1/2 nucleic acid molecules. The limiting factors in the reaction are the amounts of primers, thermostable enzyme, and nucleoside triphosphates present in the reaction. The cycling steps (i.e., denaturation, annealing, and extension) are preferably repeated at least once. For use in detection, the number of cycling steps will depend, e.g., on the nature of the sample. If the sample is a complex mixture of nucleic acids, more cycling steps will be required to amplify the target sequence sufficient for detection. Generally, the cycling steps are repeated at least about 20 times, but may be repeated as many as 40, 60, or even 100 times.

Fluorescence Resonance Energy Transfer (FRET)

FRET technology (see, for example, U.S. Pat. Nos. 4,996,143, 5,565,322, 5,849,489, and 6,162,603) is based on a concept that when a donor fluorescent moiety and a corresponding acceptor fluorescent moiety are positioned within a certain distance of each other, energy transfer takes place between the two fluorescent moieties that can be visualized or otherwise detected and/or quantitated. The donor typically transfers the energy to the acceptor when the donor is excited by light radiation with a suitable wavelength. The acceptor typically re-emits the transferred energy in the form of light radiation with a different wavelength.

In one example, a oligonucleotide probe can contain a donor fluorescent moiety and a corresponding quencher, which dissipates the transferred energy in a form other than light. When the probe is intact, energy transfer typically occurs between the two fluorescent moieties such that fluorescent emission from the donor fluorescent moiety is quenched. During an extension step of a polymerase chain reaction, a probe bound to an amplification product is cleaved by the 5' to 3' exonuclease activity of, e.g., a Taq Polymerase such that the fluorescent emission of the donor fluorescent moiety is no longer quenched. Exemplary probes for this purpose are described in, e.g., U.S. Pat. Nos. 5,210,015, 5,994,056, and 6,171,785. Commonly used donor-acceptor pairs include the FAM-TAMRA pair. Commonly used quenchers are DABCYL and TAMRA. Commonly used dark quenchers include BlackHole Quenchers™ (BHQ), (Biosearch Technologies, Inc., Novato, Cal.), Iowa Black™, (Integrated DNA Tech., Inc., Coralville, Iowa), BlackBerry™ Quencher 650 (BBQ-650), (Berry & Assoc., Dexter, Mich.).

In another example, two oligonucleotide probes, each containing a fluorescent moiety, can hybridize to an amplification product at particular positions determined by the complementarity of the oligonucleotide probes to the HSV-1/2 target nucleic acid sequence. Upon hybridization of the oligonucleotide probes to the amplification product nucleic acid at the appropriate positions, a FRET signal is generated. Hybridization temperatures can range from about 35° C. to about 65° C. for about 10 sec to about 1 min.

Fluorescent analysis can be carried out using, for example, a photon counting epifluorescent microscope system (containing the appropriate dichroic mirror and filters for monitoring fluorescent emission at the particular range), a photon counting photomultiplier system, or a fluorometer. Excitation to initiate energy transfer can be carried out with an argon ion laser, a high intensity mercury (Hg) arc lamp, a fiber optic light source, or other high intensity light source appropriately filtered for excitation in the desired range.

As used herein with respect to donor and corresponding acceptor fluorescent moieties "corresponding" refers to an acceptor fluorescent moiety having an emission spectrum that overlaps the excitation spectrum of the donor fluorescent moiety. The wavelength maximum of the emission spectrum of the acceptor fluorescent moiety should be at least 100 nm greater than the wavelength maximum of the excitation spectrum of the donor fluorescent moiety. Accordingly, efficient non-radiative energy transfer can be produced therebetween.

Fluorescent donor and corresponding acceptor moieties are generally chosen for (a) high efficiency Forster energy transfer; (b) a large final Stokes shift (>100 nm); (c) shift of the emission as far as possible into the red portion of the visible spectrum (>600 nm); and (d) shift of the emission to a higher wavelength than the Raman water fluorescent emission produced by excitation at the donor excitation wavelength. For example, a donor fluorescent moiety can be chosen that has its excitation maximum near a laser line (for example, Helium-Cadmium 442 nm or Argon 488 nm), a high extinction coefficient, a high quantum yield, and a good overlap of its fluorescent emission with the excitation spectrum of the corresponding acceptor fluorescent moiety. A corresponding acceptor fluorescent moiety can be chosen that has a high extinction coefficient, a high quantum yield, a good overlap of its excitation with the emission of the donor fluorescent moiety, and emission in the red part of the visible spectrum (>600 nm).

Representative donor fluorescent moieties that can be used with various acceptor fluorescent moieties in FRET technology include fluorescein, Lucifer Yellow, B-phycoerythrin, 9-acridineisothiocyanate, Lucifer Yellow VS, 4-acetamido-4'-isothio-cyanatostilbene-2,2'-disulfonic acid, 7-diethylamino-3-(4'-isothiocyanatophenyl)-4-methylcoumarin, succinimyl 1-pyrenebutyrate, and 4-acetamido-4'-isothiocyanatostilbene-2,2'-disulfonic acid derivatives. Representative acceptor fluorescent moieties, depending upon the donor fluorescent moiety used, include LC Red 640, LC Red 705, Cy5, Cy5.5, Lissamine rhodamine B sulfonyl chloride, tetramethyl rhodamine isothiocyanate, rhodamine x isothiocyanate, erythrosine isothiocyanate, fluorescein, diethylenetriamine pentaacetate, or other chelates of Lanthanide ions (e.g., Europium, or Terbium). Donor and acceptor fluorescent moieties can be obtained, for example, from Molecular Probes (Junction City, Oreg.) or Sigma Chemical Co. (St. Louis, Mo.).

The donor and acceptor fluorescent moieties can be attached to the appropriate probe oligonucleotide via a linker arm. The length of each linker arm is important, as the linker arms will affect the distance between the donor and acceptor fluorescent moieties. The length of a linker arm for the purpose of the present invention is the distance in Angstroms (Å) from the nucleotide base to the fluorescent moiety. In general, a linker arm is from about 10 Å to about 25 Å. The linker arm may be of the kind described in WO 84/03285. WO 84/03285 also discloses methods for attaching linker arms to a particular nucleotide base, and also for attaching fluorescent moieties to a linker arm.

An acceptor fluorescent moiety such as an LC Red 640-NHS-ester can be combined with C6-Phosphoramidites (available from ABI (Foster City, Calif.) or Glen Research (Sterling, Va.)) to produce, for example, LC Red 640-Phosphoramidite. Frequently used linkers to couple a donor fluorescent moiety such as fluorescein to an oligonucleotide include thiourea linkers (FITC-derived, for example, fluorescein-CPG's from Glen Research or ChemGene (Ashland, Mass.)), amide-linkers (fluorescein-NHS-ester-derived, such as fluorescein-CPG from BioGenex (San Ramon, Calif.)), or 3'-amino-CPGs that require coupling of a fluorescein-NHS-ester after oligonucleotide synthesis.

Detection of Herpes Simplex Virus 1 and/or 2

The present invention provides methods for detecting the presence or absence of HSV-1 and/or HSV-2 in a biological or non-biological sample. Methods provided by the invention avoid problems of sample contamination, false negatives, and false positives. The methods include performing at least one cycling step that includes amplifying a portion of HSV-1 and/or HSV-2 target nucleic acid molecules from a sample using a plurality of pairs of HSV-1 Pol, HSV-1 TK, HSV-2 TK, and HSV-2 gB primers, and a FRET detecting step. Multiple cycling steps are performed, preferably in a thermocycler. Methods of the invention can be performed using the HSV-1 and HSV-2 primers and probes to detect the presence of HSV-1 and/or HSV-2, and the detection of HSV-1 and/or HSV-2 indicates the presence of HSV-1 and/or HSV-2 in the sample.

As described herein, amplification products can be detected using labeled hybridization probes that take advantage of FRET technology. One FRET format utilizes TaqMan® technology to detect the presence or absence of an amplification product, and hence, the presence or absence of HSV-1 and/or HSV-2. TaqMan® technology utilizes one single-stranded hybridization probe labeled with two fluorescent moieties. When a first fluorescent moiety is excited with light of a suitable wavelength, the absorbed energy is transferred to a second fluorescent moiety according to the principles of FRET. The second fluorescent moiety is generally a quencher molecule. During the annealing step of the PCR reaction, the labeled hybridization probe binds to the target DNA (i.e., the amplification product) and is degraded by the 5' to 3' exonuclease activity of the Taq Polymerase during the subsequent elongation phase. As a result, the excited fluorescent moiety and the quencher moiety become spatially separated from one another. As a consequence, upon excitation of the first fluorescent moiety in the absence of the quencher, the fluorescence emission from the first fluorescent moiety can be detected. By way of example, an ABI PRISM® 7700 Sequence Detection System (Applied Biosystems) uses TaqMan® technology, and is suitable for performing the methods described herein for detecting the presence or absence of HSV-1 and/or HSV-2 in the sample.

Molecular beacons in conjunction with FRET can also be used to detect the presence of an amplification product using the real-time PCR methods of the invention. Molecular beacon technology uses a hybridization probe labeled with a first fluorescent moiety and a second fluorescent moiety. The second fluorescent moiety is generally a quencher, and the fluorescent labels are typically located at each end of the probe. Molecular beacon technology uses a probe oligonucleotide having sequences that permit secondary structure formation (e.g., a hairpin). As a result of secondary structure formation within the probe, both fluorescent moieties are in spatial proximity when the probe is in solution. After hybridization to the target nucleic acids (i.e., amplification products), the secondary structure of the probe is disrupted and the fluorescent moieties become separated from one another such that after excitation with light of a suitable wavelength, the emission of the first fluorescent moiety can be detected.

Another common format of FRET technology utilizes two hybridization probes. Each probe can be labeled with a different fluorescent moiety and are generally designed to hybridize in close proximity to each other in a target DNA molecule (e.g., an amplification product). A donor fluorescent moiety, for example, fluorescein, is excited at 470 nm by the light source of the LightCycler® Instrument. During FRET, the fluorescein transfers its energy to an acceptor fluorescent moiety such as LightCycler®-Red 640 (LC Red 640) or LightCycler®-Red 705 (LC Red 705). The acceptor fluorescent moiety then emits light of a longer wavelength, which is detected by the optical detection system of the LightCycler® instrument. Efficient FRET can only take place when the fluorescent moieties are in direct local proximity and when the emission spectrum of the donor fluorescent moiety overlaps with the absorption spectrum of the acceptor fluorescent moiety. The intensity of the emitted signal can be correlated with the number of original target DNA molecules (e.g., the number of HSV1/2 genomes). If amplification of HSV-1/2 target nucleic acid occurs and an amplification product is produced, the step of hybridizing results in a detectable signal based upon FRET between the members of the pair of probes.

Generally, the presence of FRET indicates the presence of HSV-1 and/or HSV-2 in the sample, and the absence of FRET indicates the absence of HSV-1 and/or HSV-2 in the sample. Inadequate specimen collection, transportation delays, inappropriate transportation conditions, or use of certain collection swabs (calcium alginate or aluminum shaft) are all conditions that can affect the success and/or accuracy of a test result, however. Using the methods disclosed herein, detection of FRET within, e.g., 45 cycling steps is indicative of an HSV-1 and/or HSV-2 infection.

Representative biological samples that can be used in practicing the methods of the invention include, but are not limited to dermal swabs, nasal swabs, wound swabs, blood cultures, skin, and soft tissue infections. Collection and storage methods of biological samples are known to those of skill in the art. Biological samples can be processed (e.g., by nucleic acid extraction methods and/or kits known in the art) to release HSV-1/2 nucleic acid or in some cases, the biological sample can be contacted directly with the PCR reaction components and the appropriate oligonucleotides.

Melting curve analysis is an additional step that can be included in a cycling profile. Melting curve analysis is based on the fact that DNA melts at a characteristic temperature called the melting temperature (Tm), which is defined as the temperature at which half of the DNA duplexes have separated into single strands. The melting temperature of a DNA depends primarily upon its nucleotide composition. Thus, DNA molecules rich in G and C nucleotides have a higher Tm than those having an abundance of A and T nucleotides. By detecting the temperature at which signal is lost, the melting temperature of probes can be determined. Similarly, by detecting the temperature at which signal is generated, the annealing temperature of probes can be determined. The melting temperature(s) of the HSV-1 and HSV-2 probes from the HSV-1 and/or HSV-2 amplification products can confirm the presence or absence of HSV-1 and/or HSV-2 in the sample.

Within each thermocycler run, control samples are cycled as well. Positive control samples can amplify HSV-1/2 nucleic acid control template (other than described amplification products of target genes) using, for example, control primers and control probes. Positive control samples can also amplify, for example, a plasmid construct containing HSV-1/2 nucleic acid molecules. Such a plasmid control can be amplified internally (e.g., within the sample) or in a separate sample run side-by-side with the patients' samples. Each thermocycler run can also include a negative control that, for example, lacks HSV-1/2 template DNA. Such controls are indicators of the success or failure of the amplification, hybridization, and/or FRET reaction. Therefore, control reactions can readily determine, for example, the ability of primers to anneal with sequence-specificity and to initiate elongation, as well as the ability of probes to hybridize with sequence-specificity and for FRET to occur.

In an embodiment, the methods of the invention include steps to avoid contamination. For example, an enzymatic method utilizing uracil-DNA glycosylase is described in U.S. Pat. Nos. 5,035,996, 5,683,896 and 5,945,313 to reduce or eliminate contamination between one thermocycler run and the next.

Conventional PCR methods in conjunction with FRET technology can be used to practice the methods of the invention. In one embodiment, a LightCycler® instrument is used. The following patent applications describe real-time PCR as used in the LightCycler® technology: WO 97/46707, WO 97/46714, and WO 97/46712.

The LightCycler® can be operated using a PC workstation and can utilize a Windows NT operating system. Signals from the samples are obtained as the machine positions the capillaries sequentially over the optical unit. The software can display the fluorescence signals in real-time immediately after each measurement. Fluorescent acquisition time is 10-100 milliseconds (msec). After each cycling step, a quantitative display of fluorescence vs. cycle number can be continually updated for all samples. The data generated can be stored for further analysis.

As an alternative to FRET, an amplification product can be detected using a double-stranded DNA binding dye such as a fluorescent DNA binding dye (e.g., SYBR® Green or SYBR® Gold (Molecular Probes)). Upon interaction with the double-stranded nucleic acid, such fluorescent DNA binding dyes emit a fluorescence signal after excitation with light at a suitable wavelength. A double-stranded DNA binding dye such as a nucleic acid intercalating dye also can be used. When double-stranded DNA binding dyes are used, a melting curve analysis is usually performed for confirmation of the presence of the amplification product.

It is understood that the embodiments of the present invention are not limited by the configuration of one or more commercially available instruments.

Articles of Manufacture/Kits

Embodiments of the present invention further provides for articles of manufacture or kits to detect HSV-1 and/or HSV-2. An article of manufacture can include primers and probes used to detect HSV-1 and/or HSV-2, together with suitable packaging materials. Representative primers and probes for detection of HSV-1 and/or HSV-2 are capable of hybridizing to HSV-1 and/or HSV-2 target nucleic acid molecules. In addition, the kits may also include suitably packaged reagents and materials needed for DNA immobilization, hybridization, and detection, such solid supports, buffers, enzymes, and DNA standards. Methods of designing primers and probes are disclosed herein, and representative examples of primers and probes that amplify and hybridize to HSV-1 and/or HSV-2 target nucleic acid molecules are provided.

Articles of manufacture of the invention can also include one or more fluorescent moieties for labeling the probes or, alternatively, the probes supplied with the kit can be labeled. For example, an article of manufacture may include a donor and/or an acceptor fluorescent moiety for labeling the HSV-1 and/or HSV-2 probes. Examples of suitable FRET donor fluorescent moieties and corresponding acceptor fluorescent moieties are provided above.

Articles of manufacture can also contain a package insert or package label having instructions thereon for using the HSV-1 and/or HSV-2 primers and probes to detect HSV-1 and/or HSV-2 in a sample. Articles of manufacture may additionally include reagents for carrying out the methods disclosed herein (e.g., buffers, polymerase enzymes, co-factors, or agents to prevent contamination). Such reagents may be specific for one of the commercially available instruments described herein.

Embodiments of the present invention will be further described in the following examples, which do not limit the scope of the invention described in the claims.

EXAMPLES

The following examples and figures are provided to aid the understanding of the present invention, the true scope of which is set forth in the appended claims. It is understood that modifications can be made in the procedures set forth without departing from the spirit of the invention.

Example I

Determination of HSV PCR Target Regions and Design of HSV Primers and Probes

HSV-1 was completely sequenced in 1988 (McGeoch, et al., J. Gen. Virol. 1988 July; 69 (Pt 7):1531-74) and HSV-2 was sequenced in 1998 (Dolan, et al., J. Virol. 1998 March; 72(3):2010-21). The two closest herpes viruses share the same genomic structure and the numbers of genes. HSV-1 has a 68.3% G+C content, while HSV-2 has a slightly higher 70.4% G+C content. However, their noncoding regions ($R_L$ and $R_S$; ~72-80%) have much higher percentages of G+C content than the coding regions ($U_L$ and $U_S$; ~64-69%). The homologous sequences between the two viral types vary among regions. For example, $R_L$ and $R_S$ regions have more diverse sequences, while $U_L$ and $U_S$ regions share high homologous sequences (83%).

There are a number of criteria for selection of PCR target regions. First, it is ideal to have a balanced G+C content (~50%) in target regions, such that they are easily accessible for binding to PCR primers as well as amplification, particularly when PCR thermal cycling conditions are fixed at relatively low temperatures. Second, it is preferable to have relatively large numbers of published target sequences available in public domains in order to achieve the maximum assay inclusivity. Third, depending on assay requirements, high homologous regions should be selected when an assay is required to cover different genotypes or strains, while low homologous regions should be used when an assay is required to discriminate different genotypes or strains.

The new HSV PCR assay requires amplifying both HSV-1 and HSV-2 types and distinguishing them in a single PCR reaction. Therefore, the PCR targeted genes or regions should have a low percentage of G-FC content, which is not easy to find due to the high percentage of G+C contents in HSV-1/2 genomes. Moreover, the sequence homology between viral types in the target genes or regions should be low, which allows the design of type specific primers and probes without cross reactivity. Unfortunately, although some of genes or regions in HSV genomes have a low percentage of G+C % content, they always share high homologous sequences between the two viral types. Therefore, a careful balance between the two requirements should be considered when selecting HSV PCR targets. Based on those considerations, three HSV genes are selected as PCR target genes, glycoprotein B (gB, $U_L27$), DNA polymerase (Pol, $U_L30$), and thymidine kinase (TK, $U_L23$). Those genes are located in the $U_L$ region.

Although the three target genes have relatively low percentages of G+C content, the G+C content is not evenly distributed in their sequences. Therefore, due to high sequence homologies between two viral types the entire gene sequences for both HSV viral types were carefully examined for potential PCR target regions. In addition, the regions with stretches of G or C were avoided because of potential primer cross reactivity and technical difficulty for oligo synthesis.

Secondary structures can affect amplification efficiency. Therefore, the potential secondary structure formation of all selected regions was simulated using a PCR modeling program (Visual OMPTM, DNA Software, Inc., 334 East Washington Street, Ann Arbor, Mich. 48104) under the proposed PCR conditions. Some regions, such as gB5, Pol-C, TK-A, and TK-B, have extensive hairpin structures, which may hinder the potential difficulties for amplifying.

After selection of potential PCR target regions in the three HSV genes, PCR primers and probes were carefully designed. There are two different approaches to design primers and probes to amplify both HSV types and distinguish them in a single PCR reaction. One is to design totally independent and specific PCR primers and probes for each HSV viral type. Advantage of this approach is that PCR amplification and detection are very specific for each type. But, it needs many more primers in PCR reaction, which is particularly true for a dual target PCR assay. Another approach is to design common primers to amplify both viral types, but have viral type specific probes to detect and distinguish both viral types. This approach requires fewer PCR primers, but may cause target competition issues. When designing HSV primers and probes, both approaches were used.

A total of over 160 primers and probes were designed and evaluated. For the viral type specific approach, whenever possible, primers and probes were designed at the locations where most mismatches between viral types are present, while for the common primer approach, primers were placed under homologous sequences between two viral types and probes were located under heterologous sequences. To maximize the ability to discriminate between HSV-1 and HSV-2, the mismatches in primers were placed near the 3' ends, while the mismatches in probes were placed between reporter and quencher dyes. Designing new primer and probe was done by a manual process in order to maximize the number of mismatches under primers and probes between viral types. To improve amplification specificity, an alkyl group such as a t-butyl-benzyl moeity was added to one or more nucleotides (normally A or C nucleotide at or near the 3'-terminus of primers). To facilitate identification of HSV-1 and HSV-2, the virus-specific probes are labeled with different fluorescent reporter dyes (FAM for HSV-1 and HEX for HSV-2) in conjunction with the non-fluorescent quencher dye BHQ-2 or RDQ-2.

Example II

Screening of HSV Primers and Probes

Multiple primers and probes were designed in each region and all of them were screened and evaluated in clean system using full length genomic DNA extracted from cultured and heat-inactivated, HSV viruses. In addition, a previous HSV assay was used as a control. The criteria for selecting primers and probes include early Ct values, high fluorescence increases, and specific PCR amplification products without non-specific amplifications. FIGS. 1A and 1B present an example of selection of primers that worked well in HSV TK-C region, while FIGS. 3A and 3B present an example of selection of primers that did not work well in a non-successful HSV TK-B region.

Figure 2:
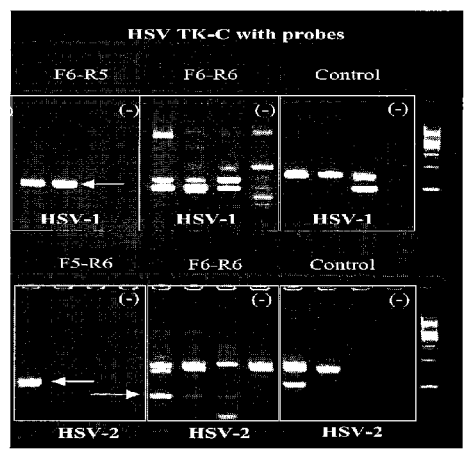
FIG. 2 shows gel electrophoresis of PCR products for HSV TK-C region.

As shown in FIG. 1A, for HSV-1 TK-C region, F6-R5 primer combination (F6: SEQ ID NO: 4; R5: SEQ ID NO: 5) worked better than F6-R6 primer combination (F6: SEQ ID NO: 4; R6: SEQ ID NO: 13) and control. As shown in FIG. 1B, for HSV-2, F5-R6 combination (F5: SEQ ID NO: 7; R6: SEQ ID NO: 8) worked better than F6-R6 combination (F6: SEQ ID NO: 14; R6: SEQ ID NO: 8). FIG. 2 shows gel electrophoresis of PCR products for HSV TK-C region. Arrows indicate the amplicon products with the right sizes. F6-R5 (F6: SEQ ID NO: 4; R5: SEQ ID NO: 5) for HSV-1 and F5-R6 (F5: SEQ ID NO: 7; R6: SEQ ID NO: 8) for HSV-2 primer combinations produced clear and right-size products, while other primer combinations showed multiple non-specific products.

Figures 3A, 3B:
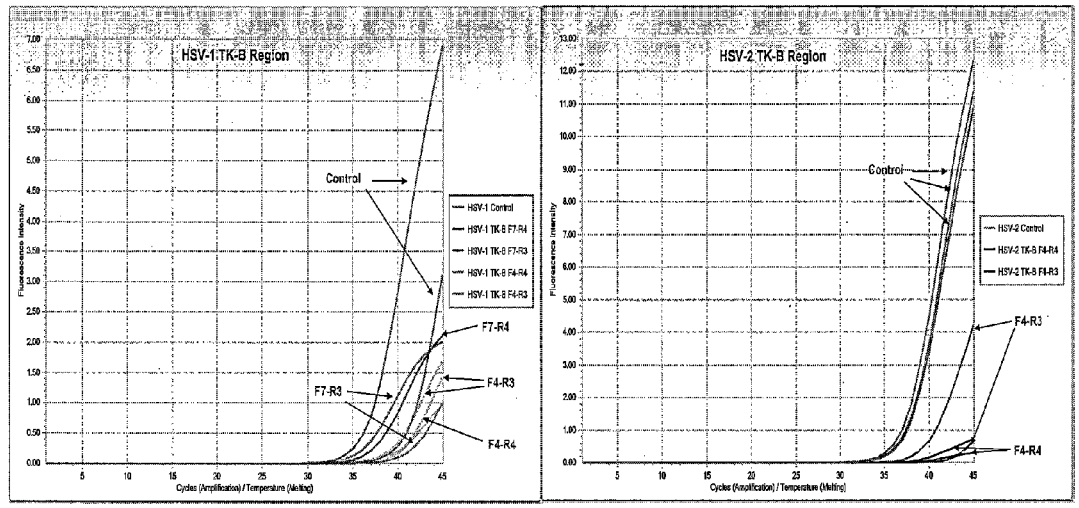
FIG. 3A shows PCR growth curves of experiments using primers for HSV-1 TK-B region.
FIG. 3B shows PCR growth curves of experiments using primers for HSV-2 TK-B region.
Figure 4:
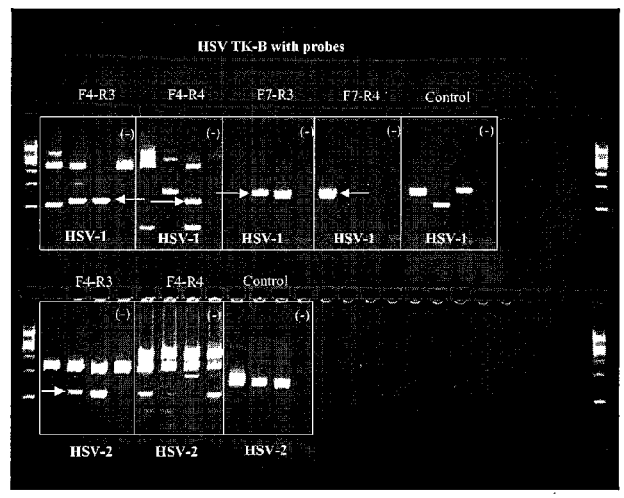
FIG. 4 shows gel electrophoresis of PCR products for HSV TK-B region.

Further experiments were performed using primers for HSV-1 TK-B region shown in FIG. 3A. FIG. 3B shows PCR growth curves experiments using primers for HSV-2 TK-B region. For HSV-1 TK-B region (FIG. 3A) and HSV-2 (FIG. 3B), none of primer combinations worked better than the control (For HSV-1, F7: SEQ ID NO: 15; R3: SEQ ID NO: 16; R4: SEQ ID NO: 17. For HSV-2, F4: SEQ ID NO: 18; R3: SEQ ID NO: 19; R4: SEQ ID NO: 20). FIG. 4 shows gel electrophoresis of PCR products for HSV TK-B region. Arrows indicate the amplicon products with the right sizes. For HSV-1, although some primer combinations (F7-R3 (F7: SEQ ID NO: 15; R3: SEQ ID NO: 16) and F7-R4 (F7: SEQ ID NO: 15; R4: SEQ ID NO: 17)) gave clear single amplification products, their growth curves were not satisfactory. For HSV-2, there were multiple non-specific products besides the right size products.

Figure 5:
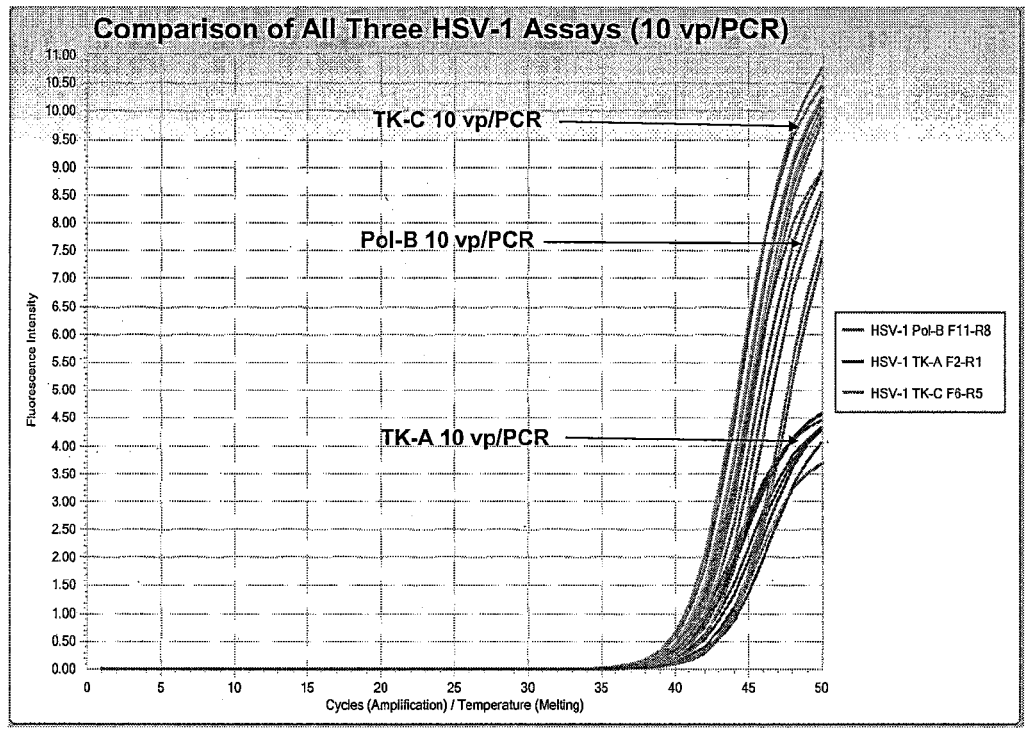
FIG. 5 shows growth curves of three HSV-1 assays, Pol-B, TK-A, and TK-C at 10 vp (virus particle) per PCR.
Figure 6:
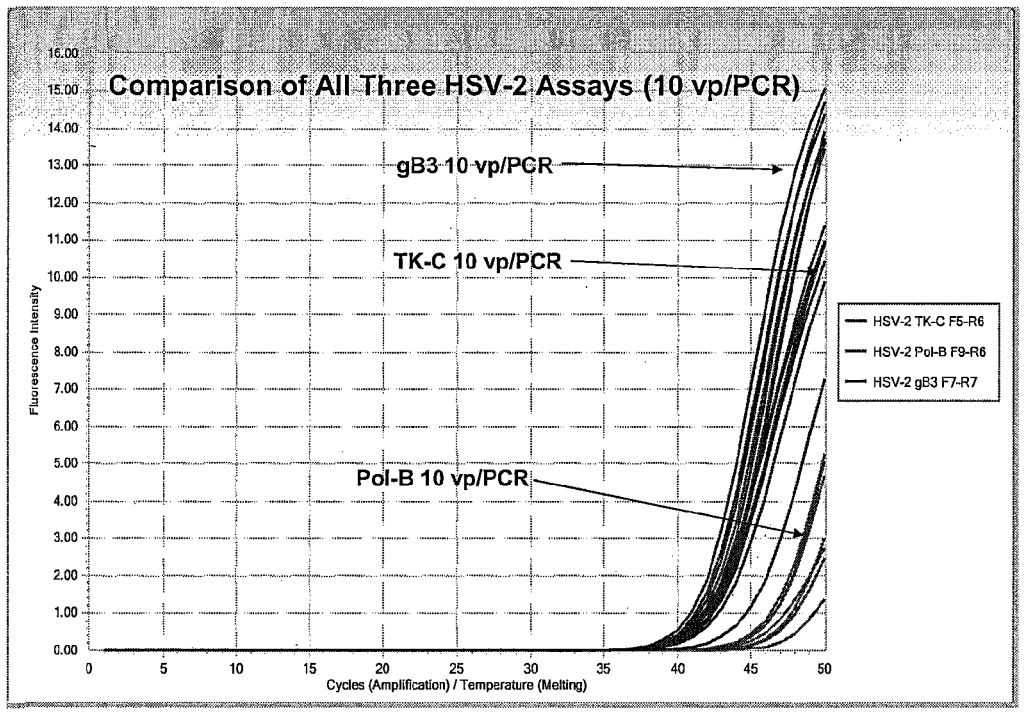
FIG. 6 shows growth curves of three HSV-2 assays, gB3, Pol-B, and TK-C at 10 vp (virus particle) per PCR.

All primer and probe combinations in 8 regions were thoroughly evaluated as illustrated above. One primer and probe combination in three regions for each HSV-1 and HSV-2 virus type were selected for further evaluation of assay performance and comparison, such as assay analytic sensitivity. Then, the best two combinations for each virus type (Pol-B and TK-C for HSV-1; gB3 and TK-C for HSV-2) were finally chosen for a dual-target HSV assay. FIG. 5 shows growth curves for HSV-1 Pol-B, F11: SEQ ID NO: 1; R8: SEQ ID NO: 2; for HSV-1 TK-A, F2: SEQ ID NO: 21; R1: SEQ ID NO: 22; and for HSV-1 TK-C, F6: SEQ ID NO: 4; R5: SEQ ID NO: 5). FIG. 6 shows growth curves for HSV-2 TK-C, F5: SEQ ID NO: 7; R6: SEQ ID NO: 8; for HSV-2 Pol-B, F9: SEQ ID NO: 23; R6: SEQ ID NO: 24; and for HSV-2 gB3, F7: SEQ ID NO: 10; R7: SEQ ID NO: 11.

Separate experiments were performed for analytical sensitivity analysis. FIG. 7 shows the results for three independent HSV-1 assays (Pol-B, TK-A, and TK-C). Prob indicates Probability and vp/PCR indicates Limit of Detection per PCR, while l95_conc and u95_conc refer to 95% Lower Confidence Limit and 95% Upper Confidence Limit, respectively. FIG. 8 shows the results for three independent HSV-2 assays (gB3, Pol-B, and TK-C). Prob indicates Probability and vp/PCR indicates Limit of Detection per PCR, while l95_conc and u95_conc refer to 95% Lower Confidence Limit and 95% Upper Confidence Limit, respectively.

The final selection of the 4 regions for HSV-1 and HSV-2 was very consistent to the analysis of those regions in silico. For example, among all 8 regions, the final selected 4 regions have the lowest percentages of G+C contents and fewer long hairpin secondary structures than other regions, which make them very accessible under a fixed PCR thermal profile.

Example III

Target Competition

Figure 11A:
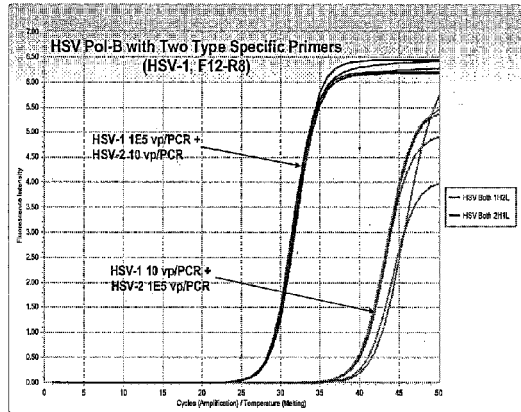
FIGS. 11A and 11B show target competition with type specific PCR primers in presence of both targets.
Figure 11B:
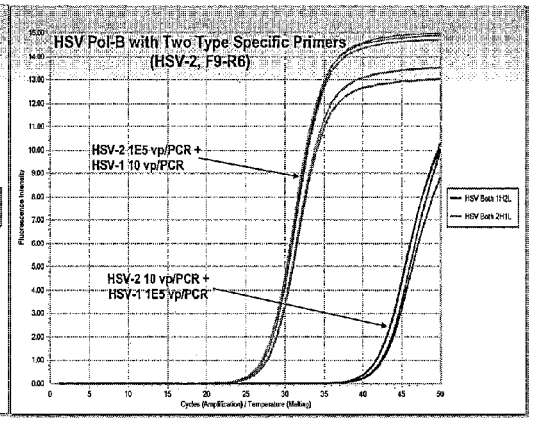

As mentioned earlier, two different approaches can be used to design HSV primers and probes to detect and discriminate HSV-1 and HSV-2 viruses. Common PCR primers to amplify both viral targets were first designed in the HSV Pol-B region. The discrimination of viral types was achieved by viral type specific probes. However, during the primer evaluation, it was found that when both viral targets are present in a single PCR reaction, the target with a lower copy number may be competed out by the target with a higher copy number. Although the cause of this phenomenon is not clear, it is speculated that the common PCR primers may cause this imbalanced target amplifications. FIGS. 9A and 9B illustrate the phenomenon (For HSV-1 and HSV-2 Pol-B, F4: SEQ ID NO: 25; R5: SEQ ID NO: 26). When common primers were used and both HSV viral types were present in a PCR reaction, the target with a lower copy number (10 viral particles per PCR) was competed out by another target with a higher copy number (1000 viral particles per PCR). When one of the two common primers, in this case the reverse primer, was replaced with viral type specific primers, the target competition still exists, but with less severity (FIGS. 10A and 10B) (For HSV-1 Pol-B, F4: SEQ ID NO: 27; R8: SEQ ID NO: 2. For HSV-2 Pol-B, F4: SEQ ID NO: 27; R6: SEQ ID NO: 28). When both common primers were completely replaced with viral type specific primers in the same region, no target competition was observed at up to 10,000-folds target concentration differences in those reactions (FIGS. 11A and 11B) (For HSV-1 Pol-B, F12: SEQ ID NO: 29; R8: SEQ ID NO: 2. For HSV-2 Pol-B, F9: SEQ ID NO: 23; R6: SEQ ID NO: 24).

Detection and discrimination of both HSV-1 and HSV-2 in a single PCR reaction without target competition offer the superior assay performance over other HSV PCR assays that are reported or on the market so far. It not only uses one reaction tube and a single sample, but also is sensitive and viral type specific. As a result, all of HSV target amplification primers and detection probes were designed and selected to be viral type specific.

Example IV

Cross Reactivity

Figure 12A:
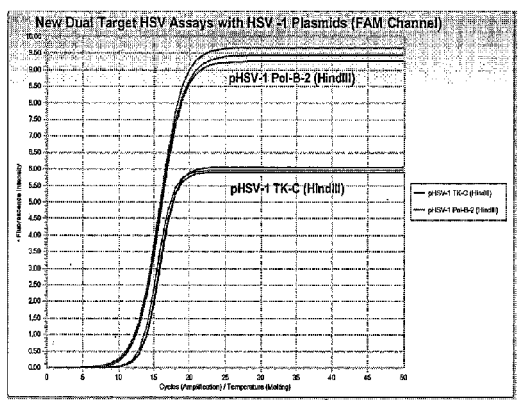
FIGS. 12A and 12B show cross reactivity analysis of the dual target HSV-1/2 assay with HSV-1 plasmids.
Figure 12B:
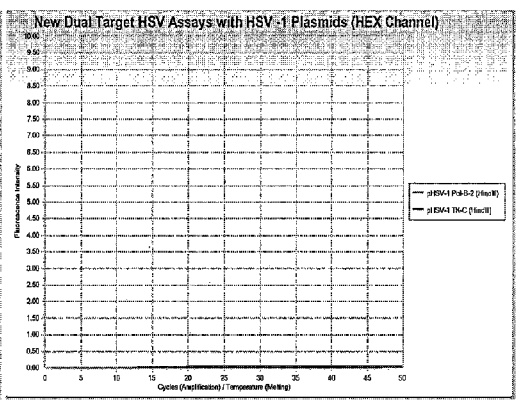

Designing viral type specific primers and probes to maximize their specificity posed challenges due to the high degree of sequence homologies between HSV-1 and HSV-2. Experiments have been carried out to examine the potential cross reactivity of the primers and probes. In those experiments, the primers and probes were challenged with the high concentrations of plasmids that contain the target regions of the opposite viral types. As shown in FIGS. 12A and 12B, two plasmids (cut by Hind III) containing the HSV-1 Pol-B and HSV-1 TK-C regions, respectively (pHSV-1 Pol-B-2 and pHSV-1 TK-C), were amplified by the newly designed HSV dual target assay. As expected, positive signals were only observed in the FAM channel (FIG. 12A) and not in the HEX channel (FIG. 12B). Similarly, two HSV-2 plasmids (cut by Hind III) containing HSV-2 gB3 and HSV-2 TK-C regions, respectively (pHSV-2 gB3 and pHSV-2 TK-C), were amplified by the newly designed HSV dual target assay. As expected, positive signals were only observed in the HEX (FIG. 13B) channel and not in the FAM channel (FIG. 13A).

In addition to the potential cross reactivity between HSV-1 and HSV-2 viral types, the newly designed dual target HSV-1/2 assay was also challenged with high concentrations of other closely related herpes viruses from the same family. As shown in FIG. 14, the new HSV-1/2 assay has no cross reactivity with other closely related herpes viruses.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed:

1. A method of detecting and discriminating HSV-1 and HSV-2 in a sample in a single PCR reaction, the method comprising:
performing an amplifying step comprising contacting the sample with two sets of HSV-1 specific primers to produce amplification products from two HSV-1 gene targets, if any HSV-1 nucleic acid is present in the sample; and two sets of HSV-2 specific primers to produce amplification products from two HSV-2 gene targets, if any HSV-2 nucleic acid is present in the sample;
performing a hybridizing step comprising contacting said amplification products from said two HSV-1 gene targets and from said two HSV-2 gene targets with two detectable HSV-1 probes, one for each HSV-1 gene target, and two detectable HSV-2 probes, one for each HSV-2 gene target; and
detecting the presence or absence of said amplification products from said two HSV-1 gene targets and from said two HSV-2 gene targets, wherein the presence of said amplification products from said two HSV-1 gene targets and from said two HSV-2 gene targets is indicative of the presence of HSV-1 and/or HSV-2 in the sample and wherein the absence of said amplification products from said two HSV-1 gene targets and from said two HSV-2 gene targets is indicative of the absence of HSV-1 and/or HSV-2 in the sample;
wherein said amplifying, hybridizing and detecting steps are performed in a single PCR reaction wherein a DNA polymerase having 5' to 3' exonuclease activity cleaves a fluorogenic probe hybridized to the amplification products during the PCR reaction, resulting in increased fluorescence, and
wherein said two sets of HSV-1 specific primers and two sets of HSV-2 specific primers comprise:
HSV-1 specific primer sets that comprise nucleic acid sequences of SEQ ID NOs: 1 and 2 or a complement thereof, that specifically amplify an HSV-1 DNA polymerase B (HSV-1 Pol) gene and that does not amplify an HSV-2 DNA polymerase (HSV-2 Pol) gene and HSV-1 specific primer sets that comprise nucleic acid sequences of SEQ ID NOs: 4 and 5 or a complement thereof, that specifically amplify an HSV-1 thymidine kinase C (HSV-1 TK) gene and that does not amplify an HSV-2 thymidine kinase C (HSV-2 TK) gene;
HSV-2 specific primer sets that comprise nucleic acid sequences of SEQ ID NOs: 7 and 8 or a complement thereof, that specifically amplify the HSV-2 TK gene and that does not amplify the HSV-1 TK gene and HSV-2 specific primer sets that comprise nucleic acid sequences of SEQ ID NOs: 10 and 11 or a complement thereof, that specifically amplify an HSV-2 glycoprotein B (HSV-2 gB) gene and that does not amplify an HSV-1 glycoprotein B (HSV-1 gB) gene,
wherein no target competition is observed at up to 10,000-folds target concentration differences between HSV-1 and HSV-2; and
wherein said two detectable HSV-1 and two HSV-2 probes comprise:
a detectable HSV-1 probe comprising the nucleic acid sequence of SEQ ID NO:3 or a complement thereof that is specific for an HSV-1 Pol amplification product, and a detectable HSV-1 probe comprising the nucleic acid sequence of SEQ ID NO: 6 or a complement thereof that is specific for an HSV-1 TK amplification product; and
a detectable HSV-2 probes comprising the nucleic acid sequence of SEQ ID NO: 9 or a complement thereof that is specific for an HSV-2 TK amplification product, and a detectable HSV-2 probe comprising the nucleic acid sequence of SEQ ID NO: 12 or a complement thereof that is specific for an HSV-2 gB amplification product.

2. The method of claim 1, wherein each of the two detectable HSV-1 probes and two detectable HSV-2 probes is labeled with a donor fluorescent moiety and a corresponding acceptor fluorescent moiety; and
wherein the detecting step comprises detecting the presence or absence of fluorescence resonance energy transfer (FRET) between the donor fluorescent moiety and the acceptor fluorescent moiety of the two HSV-1 probes and/or two HSV-2 probes, wherein the presence or absence of fluorescence is indicative of the presence or absence of HSV-1 and/or HSV-2 in the sample.

3. The method of claim 2, wherein said donor and acceptor fluorescent moieties are within no more than 5 nucleotides of each other on said probe.

4. The method of claim 3, wherein said acceptor fluorescent moiety is a quencher.

* * * * *

SEQUENCE LISTING

<160> NUMBER OF SEQ ID NOS: 29

<210> SEQ ID NO 1
<211> LENGTH: 23
<212> TYPE: DNA
<213> ORGANISM: Artificial Sequence
<220> FEATURE:
<223> OTHER INFORMATION: Oligonucleotide

<400> SEQUENCE: 1
gacaacttct gcccggccat caa                                          23

<210> SEQ ID NO 2
<211> LENGTH: 22
<212> TYPE: DNA
<213> ORGANISM: Artificial Sequence
<220> FEATURE:
<223> OTHER INFORMATION: Oligonucleotide

<400> SEQUENCE: 2
tcgctggatg tcccgaaggc ca                                           22

<210> SEQ ID NO 3
<211> LENGTH: 30
<212> TYPE: DNA
<213> ORGANISM: Artificial Sequence
<220> FEATURE:

<223> OTHER INFORMATION: Oligonucleotide

<400> SEQUENCE: 3
cggaacaaca cgctagccca gccgcgggcc                                    30

<210> SEQ ID NO 4
<211> LENGTH: 27
<212> TYPE: DNA
<213> ORGANISM: Artificial Sequence
<220> FEATURE:
<223> OTHER INFORMATION: Oligonucleotide

<400> SEQUENCE: 4
cgtctttatc ctggattacg accaatc                                       27

<210> SEQ ID NO 5
<211> LENGTH: 22
<212> TYPE: DNA
<213> ORGANISM: Artificial Sequence
<220> FEATURE:
<223> OTHER INFORMATION: Oligonucleotide

<400> SEQUENCE: 5
ggtcgcagat cgtcggtatg ga                                            22

<210> SEQ ID NO 6
<211> LENGTH: 30
<212> TYPE: DNA
<213> ORGANISM: Artificial Sequence
<220> FEATURE:
<223> OTHER INFORMATION: Oligonucleotide

<400> SEQUENCE: 6
ctgcaactta cctccgggat ggtccagacc                                    30

<210> SEQ ID NO 7
<211> LENGTH: 24
<212> TYPE: DNA
<213> ORGANISM: Artificial Sequence
<220> FEATURE:
<223> OTHER INFORMATION: Oligonucleotide

<400> SEQUENCE: 7
tccttccgat gcatctattt gtcc                                          24

<210> SEQ ID NO 8
<211> LENGTH: 19
<212> TYPE: DNA
<213> ORGANISM: Artificial Sequence
<220> FEATURE:
<223> OTHER INFORMATION: Oligonucleotide

<400> SEQUENCE: 8
atggacccgg cggttgtga                                                19

<210> SEQ ID NO 9
<211> LENGTH: 29
<212> TYPE: DNA
<213> ORGANISM: Artificial Sequence
<220> FEATURE:
<223> OTHER INFORMATION: Oligonucleotide

<400> SEQUENCE: 9
ttgcgcctca ccgccgggat gatcccaac                                     29

```
<210> SEQ ID NO 10
<211> LENGTH: 22
<212> TYPE: DNA
<213> ORGANISM: Artificial Sequence
<220> FEATURE:
<223> OTHER INFORMATION: Oligonucleotide

<400> SEQUENCE: 10
cgctacgtcc tgcaactgca ac                                              22

<210> SEQ ID NO 11
<211> LENGTH: 26
<212> TYPE: DNA
<213> ORGANISM: Artificial Sequence
<220> FEATURE:
<223> OTHER INFORMATION: Oligonucleotide

<400> SEQUENCE: 11
ggccgacacc aaagccatat atcgga                                          26

<210> SEQ ID NO 12
<211> LENGTH: 36
<212> TYPE: DNA
<213> ORGANISM: Artificial Sequence
<220> FEATURE:
<223> OTHER INFORMATION: Oligonucleotide

<400> SEQUENCE: 12
tccgctcacc accaaggaac tcaagacttc cgaccc                               36

<210> SEQ ID NO 13
<211> LENGTH: 22
<212> TYPE: DNA
<213> ORGANISM: Artificial Sequence
<220> FEATURE:
<223> OTHER INFORMATION: Oligonucleotide

<400> SEQUENCE: 13
ggtatggagc ctggggtggt ga                                              22

<210> SEQ ID NO 14
<211> LENGTH: 19
<212> TYPE: DNA
<213> ORGANISM: Artificial Sequence
<220> FEATURE:
<223> OTHER INFORMATION: Oligonucleotide

<400> SEQUENCE: 14
ccgtcgggtg tcgagacgc                                                  19

<210> SEQ ID NO 15
<211> LENGTH: 21
<212> TYPE: DNA
<213> ORGANISM: Artificial Sequence
<220> FEATURE:
<223> OTHER INFORMATION: Oligonucleotide

<400> SEQUENCE: 15
ggaggattgg ggacagcttt c                                               21

<210> SEQ ID NO 16
<211> LENGTH: 25
<212> TYPE: DNA
<213> ORGANISM: Artificial Sequence
<220> FEATURE:
<223> OTHER INFORMATION: Oligonucleotide
```

<400> SEQUENCE: 16
cccaggcaaa cacgttatac aggtc                                              25

<210> SEQ ID NO 17
<211> LENGTH: 21
<212> TYPE: DNA
<213> ORGANISM: Artificial Sequence
<220> FEATURE:
<223> OTHER INFORMATION: Oligonucleotide

<400> SEQUENCE: 17
aaggcccagg caaacacgtt a                                                  21

<210> SEQ ID NO 18
<211> LENGTH: 18
<212> TYPE: DNA
<213> ORGANISM: Artificial Sequence
<220> FEATURE:
<223> OTHER INFORMATION: Oligonucleotide

<400> SEQUENCE: 18
cccgaccccg aggacggc                                                      18

<210> SEQ ID NO 19
<211> LENGTH: 25
<212> TYPE: DNA
<213> ORGANISM: Artificial Sequence
<220> FEATURE:
<223> OTHER INFORMATION: Oligonucleotide

<400> SEQUENCE: 19
ccaggcaaaa atgtggtaca agtcc                                              25

<210> SEQ ID NO 20
<211> LENGTH: 19
<212> TYPE: DNA
<213> ORGANISM: Artificial Sequence
<220> FEATURE:
<223> OTHER INFORMATION: Oligonucleotide

<400> SEQUENCE: 20
gggaacgcgg aacagggca                                                     19

<210> SEQ ID NO 21
<211> LENGTH: 19
<212> TYPE: DNA
<213> ORGANISM: Artificial Sequence
<220> FEATURE:
<223> OTHER INFORMATION: Oligonucleotide

<400> SEQUENCE: 21
gaccaggctg cgcgttctc                                                     19

<210> SEQ ID NO 22
<211> LENGTH: 21
<212> TYPE: DNA
<213> ORGANISM: Artificial Sequence
<220> FEATURE:
<223> OTHER INFORMATION: Oligonucleotide

<400> SEQUENCE: 22
cggacttccg tggcttcttg c                                                  21

<210> SEQ ID NO 23
<211> LENGTH: 21

```
<212> TYPE: DNA
<213> ORGANISM: Artificial Sequence
<220> FEATURE:
<223> OTHER INFORMATION: Oligonucleotide

<400> SEQUENCE: 23
cttttgcccc gcgatcagga a                                         21

<210> SEQ ID NO 24
<211> LENGTH: 21
<212> TYPE: DNA
<213> ORGANISM: Artificial Sequence
<220> FEATURE:
<223> OTHER INFORMATION: Oligonucleotide

<400> SEQUENCE: 24
tcgctcgagg ttccgaacgc c                                         21

<210> SEQ ID NO 25
<211> LENGTH: 19
<212> TYPE: DNA
<213> ORGANISM: Artificial Sequence
<220> FEATURE:
<223> OTHER INFORMATION: Oligonucleotide

<400> SEQUENCE: 25
gtcaccttcg gctggtacc                                            19

<210> SEQ ID NO 26
<211> LENGTH: 24
<212> TYPE: DNA
<213> ORGANISM: Artificial Sequence
<220> FEATURE:
<223> OTHER INFORMATION: Oligonucleotide

<400> SEQUENCE: 26
gtccgccgta cagttaaact cgac                                      24

<210> SEQ ID NO 27
<211> LENGTH: 19
<212> TYPE: DNA
<213> ORGANISM: Artificial Sequence
<220> FEATURE:
<223> OTHER INFORMATION: Oligonucleotide

<400> SEQUENCE: 27
gtcaccttcg gctggtacc                                            19

<210> SEQ ID NO 28
<211> LENGTH: 21
<212> TYPE: DNA
<213> ORGANISM: Artificial Sequence
<220> FEATURE:
<223> OTHER INFORMATION: Oligonucleotide

<400> SEQUENCE: 28
tcgctcgagg ttccgaacgc c                                         21

<210> SEQ ID NO 29
<211> LENGTH: 21
<212> TYPE: DNA
<213> ORGANISM: Artificial Sequence
```

-continued

```
<220> FEATURE:
<223> OTHER INFORMATION: Oligonucleotide

<400> SEQUENCE: 29
gcgacaactt ctgcccggcc a                                          21
```